(12) United States Patent
Che et al.

(10) Patent No.: US 8,957,217 B2
(45) Date of Patent: Feb. 17, 2015

(54) PHOSPHORESCENT MATERIAL, THEIR PREPARATIONS AND APPLICATIONS

(75) Inventors: Chi Ming Che, Hong Kong (CN); Kai Li, Hong Kong (CN)

(73) Assignees: The University of Hong Kong, Hong Kong (CH); Versitech Limited, Hong Kong (CH)

( * ) Notice: Subject to any disclaimer, the term of this patent is extended or adjusted under 35 U.S.C. 154(b) by 199 days.

(21) Appl. No.: 13/482,448

(22) Filed: May 29, 2012

(65) Prior Publication Data
US 2012/0309979 A1    Dec. 6, 2012

Related U.S. Application Data

(60) Provisional application No. 61/491,711, filed on May 31, 2011.

(51) Int. Cl.
| | | |
|---|---|---|
| *C07F 15/00* | (2006.01) | |
| *C09K 11/06* | (2006.01) | |
| *H01L 51/00* | (2006.01) | |
| *H05B 33/14* | (2006.01) | |
| *H01L 51/50* | (2006.01) | |

(52) U.S. Cl.
CPC ............. *C09K 11/06* (2013.01); *C07F 15/0086* (2013.01); *H01L 51/0087* (2013.01); *H05B 33/14* (2013.01); *H01L 51/5016* (2013.01); *C09K 2211/1007* (2013.01); *C09K 2211/1044* (2013.01); *C09K 2211/185* (2013.01)
USPC .......................................................... 548/103

(58) Field of Classification Search
USPC ........................................................... 548/103
See application file for complete search history.

(56) References Cited

FOREIGN PATENT DOCUMENTS

WO     WO 2006/058535    *    6/2006

OTHER PUBLICATIONS

Yagyu et al. "Synthesis and Characterization of a Manganese(III) Complex with a Tetradentate N-Heterocyclic Carbene Ligand" Organometallics, 2009, vol. 28, pp. 2342-2344.*
Li et al. "Blue electrophosphorescent organoplatinum(II) complexes with dianionic tetradentate bis(carbene) ligands" Chemical Communications, 2011, vol. 47, pp. 9075-9077 plus 20 pages of supporting information.*

* cited by examiner

*Primary Examiner* — Joseph Kosack
(74) *Attorney, Agent, or Firm* — Saliwanchik, Lloyd & Eisenchenk (57) ABSTRACT

The subject invention is directed to tetradentate bis-(NHC carbenes) alkylene ligand Pt(II) complexes, tetradentate bis-(NHC carbenes) alkylene ligands, and its ligand precursors, for preparation of the Pt(II) complexes. The Pt(II) complexes show a deep blue emission with an improved quantum efficiency and can be used for fabrication of OLEDs with an electroluminescence layer that comprise the bis-(NHC carbenes) alkylene ligand Pt(II) complexes.

11 Claims, 6 Drawing Sheets

PHOSPHORESCENT MATERIAL, THEIR PREPARATIONS AND APPLICATIONS

CROSS-REFERENCE TO RELATED APPLICATION

This application claims the benefit of U.S. Provisional Application Ser. No. 61/491,711, filed May 31, 2011, which is hereby incorporated by reference in its entirety including any tables, figures, or drawings.

FIELD OF THE INVENTION

The invention relates to a class of phosphorescent materials, their preparation methods and organic light emitting diodes (OLEDs) using these materials.

BACKGROUND OF THE INVENTION

The first organic light-emitting diode (OLED) was disclosed by Tang et. al. (U.S. Pat. No. 4,356,429) and Tang et. al. (*Appl. Phys. Lett.* 1987, 51, 12, 913). Subsequently, device architecture and emissive materials for OLED applications have been intensively studied. OLEDs allow devices that are (1) ultra-thin; (2) self-emissive; (3) use low operating voltage with high efficiency; and (4) display high contrast and resolution.

Phosphorescent materials are the primary direction of emissive material development, because these OLED devices generate 25% singlet and 75% triplet excitons. Devices fabricated from phosphorescent materials generally display efficiencies that are higher than devices fabricated from fluorescent materials. Platinum complexes are a class of emissive materials that offer high emission quantum efficiency and good thermal stability. High performance OLEDs have been formed using platinum(II) complexes. (Yan et al., *Appl. Phys. Lett.* 2007, 91(6) 063508; Che et al., *Chemistry—A European Journal* 2010, 16(1), 233)

Producing blue-emitting phosphorescent materials has proven to be challenging. However, high performance and long lifetime blue-emitting OLEDs have not been fabricated from platinum(II) complexes. To tune the emission color of platinum(II) complexes, the appropriate conjugation length of the ligand is essential. Neutral blue-emitting Pt(II) complex were prepared by coordinating two bidentate ligands to a Pt(II) center, resulting in the first blue-emitting Pt(II) complexes. (Brooks et al., *Inorg. Chem.* 2002, 41, 3055; and Unger et al., *Angew. Chem. Int. Ed.* 2010, 49, 10214) However, binding forces between these bidentate ligands and the platinum(II) center in these complexes are weaker than the binding forces of complexes containing one tetradentate ligand bound to a Pt(II). The devices that form these bisbidentate ligand Pt(II) complexes display lifetimes and stabilities that are inferior to device tetradentate Pt(II) complexes. Ligand systems having more than two aryl groups, coupled by a non-conjugated unit, do not provide emission maxima less than 480 nm. (U.S. Pat. No. 7,026,480, U.S. Pat. No. 6,653,654). Blue-emitting materials have not been made from this type of tridentate or tetradentate ligands. Efforts directed to tetradentate blue-emitting Pt(II) materials where conjugation groups connect aryl groups of the ligands, have failed to generate complexes with emission maxima less than 480 nm. (U.S. Pat. No. 7,361,415, U.S. Pat. No. 7,691,495 and U.S. Published Patent Application 2007/0103060 A1)

N-heterocyclic carbenes (NHC) are strong σ-donors but poor π-acceptors. Using cyclometalated Pt(II) complexes, Meyer et al., *Organometallics,* 2011, 30 (11), 2980 discloses Pt(II) complexes with shortened ligand π-conjugations, but does not report of the emission spectra.

BRIEF SUMMARY OF THE INVENTION

Embodiments of the invention are directed to blue phosphorescent platinum(II) complexes of dianionic tetradentate bis-(NHC carbene) ligand of structure II:

wherein $R_1$-$R_8$ are, independently, hydrogen, fluoro, chloro, bromo, iodo, hydroxyl, alkyl, substituted alkyl, cycloalkyl, substituted cycloalkyl, aryl, substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or alkoxycarbonyl, and X is, independently, oxygen, nitrogen, sulphur, phosphorus, or selenium. Other embodiments of the invention are directed to the preparation of the tetradentate bis-(NHC carbene) ligands where at least one of $R_1$-$R_8$ are not hydrogen, and OLEDs comprise Pt(II) complexes of tetradentate bis-(NHC carbene) ligands.

DETAILED DISCLOSURE OF THE INVENTION

Embodiments of the invention are directed to tetradentate ligands comprising a bis-(NHC carbenes) alkylene, as shown in the bis-anion-bis-carbene form in structure I:

(I)

wherein $R_1$-$R_8$ are, independently, hydrogen, fluoro, chloro, bromo, iodo, hydroxyl, alkyl, substituted alkyl, cycloalkyl, substituted cycloalkyl, aryl, substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or alkoxycarbonyl; and wherein at least one of $R_1$-$R_8$ is not hydrogen; and X is O, $NR_9$, S, $PR_9$, or Se, where $R_9$ is H or alky. In an embodiment of the invention, $R_6$ is not hydrogen. In an embodiment of the invention, $R_8$ is not hydrogen. Embodiments of the invention are directed to stable blue-emitting platinum(II) complexes prepared from ligands comprising bis-(NHC carbenes) where the tetradentate ligand I's electron donor substituents, X, are in anions in a Pt complex of structure II:

(II)

wherein $R_1$-$R_7$ are, independently, hydrogen, fluoro, chloro, bromo, iodo, hydroxyl, alkyl, substituted alkyl, cycloalkyl, substituted cycloalkyl, aryl, substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or alkoxycarbonyl; wherein at least one of $R_1$-$R_8$ is not hydrogen; and X is O, $NR_9$, S, $PR_9$, or Se, where $R_9$ is H or alky. In an embodiment of the invention, $R_6$ is not hydrogen. In an embodiment of the invention, $R_8$ is not hydrogen In an embodiment of the invention, the tetradentate ligand precursor is in the protonated form:

(III)

wherein $R_1$-$R_7$ are, independently, hydrogen, fluoro, chloro, bromo, iodo, hydroxyl, alkyl, substituted alkyl, cycloalkyl, substituted cycloalkyl, aryl, substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or alkoxycarbonyl; wherein at least one of $R_1$-$R_8$ is not hydrogen; X is O, $NR_9$, S, $PR_9$, or Se, where $R_9$ is H or alky; and $A^-$ is chloride, bromide, iodide, tosylate, brosylate, triflate, or other anion of low nucleophilicity. In an embodiment of the invention, $R_6$ is not hydrogen. In an embodiment of the invention, $R_8$ is not hydrogen.

Figure 1:
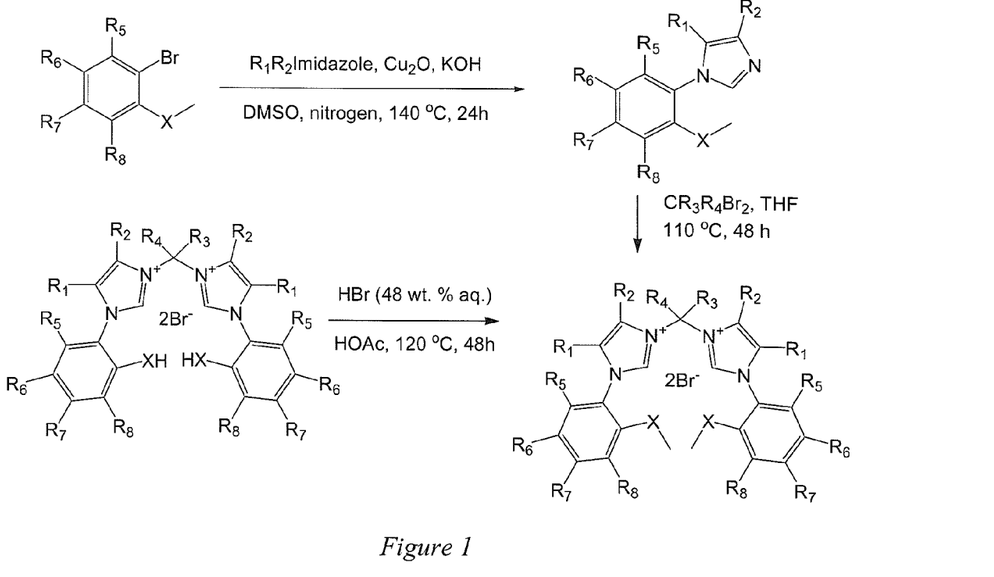
FIG. 1 shows a reaction scheme for the preparation of tetradentate bis-(NHC carbene) ligand precursors, according to an embodiment of the invention.
Figure 2:
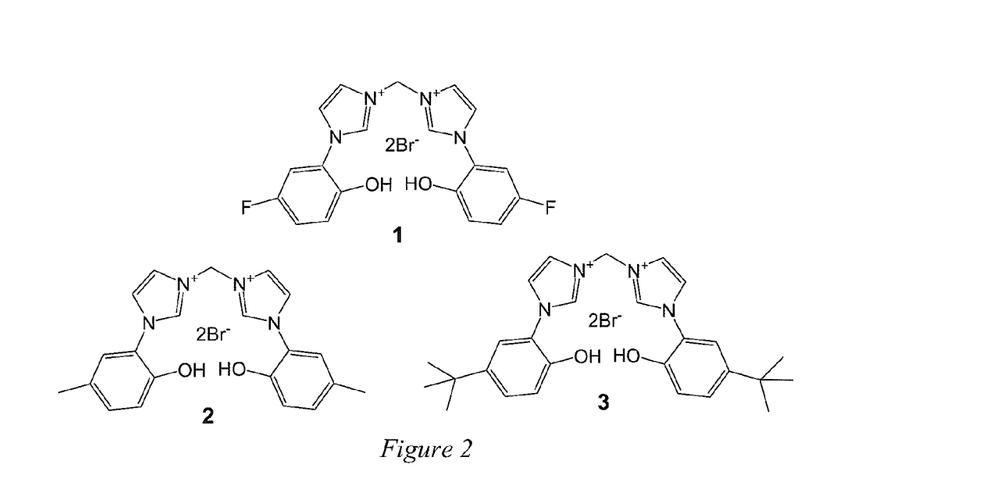
FIG. 2 shows the structure of three exemplary tetradentate bis-(NHC carbene) ligand precursors, 1-3, according to an embodiment of the invention.

Tetradentate ligand precursors III can be prepared by a series of reactions depicted in FIG. 1, where $A^-$ is $Br^-$. Synthesis occurs through reaction of an X protected o-halo substituted phenol, thiol, selenol, aniline, N-alkylaniline, phenylphosphane, or P-alkyl phenylphosphane, with imidazole, either unsubstituted, 4-substituted, or 4,5-disubstituted. The resulting N-aryl substituted imidazoles di-substitute a gem-dihaloalkane, or its functional equivalent towards nucleophilic substitution, as can be appreciated by one skilled in the art. The protected precursor is one where H of the XH is replaced with a protecting group that can be replaced with hydrogen, for example a methyl group. The reaction results in an X protected bis-(NHC carbenes) alkylene precursor, where upon deprotection, the bis-(NHC carbenes) alkylene ligand is provided as a precursor in a tetra-protonated form. Exemplary tetra-protonated bis-(NHC carbenes) alkylene ligand precursors, according to an embodiment of the invention, are shown in FIG. 2.

Figure 4:
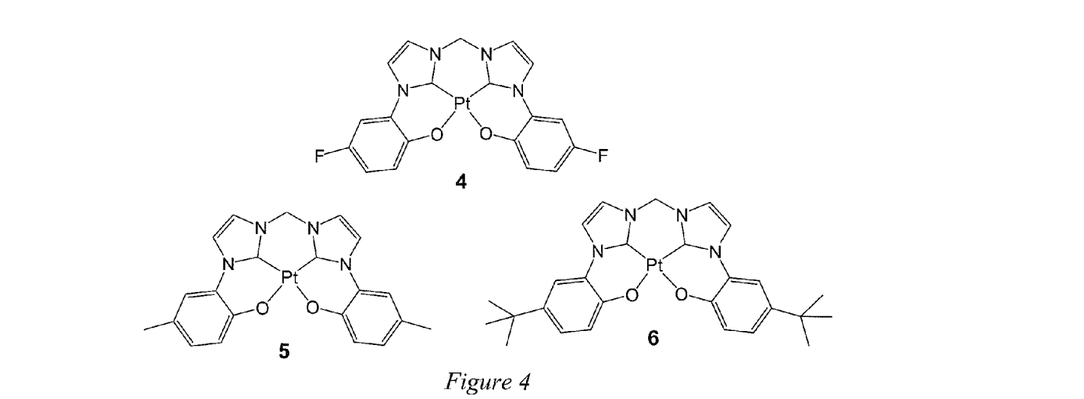
FIG. 4 shows the structure of three exemplary tetradentate bis-(NHC carbene) ligand Pt(II) complexes, 4-6, according to an embodiment of the invention.

Exemplary tetradentate bis-(NHC carbenes) alkylene ligand Pt(II) complexes, according to an embodiment of the invention, are shown in FIG. 4. In an embodiment of the invention, the tetradentate bis-(NHC carbenes) alkylene ligand Pt(II) complex displays a vibronically structured absorption band, with a peak maximum at about 350 nm and molar extinction coefficient of about $1\times10^4$ $M^{-1}$ $cm^{-1}$, and displays, in solution, a structure-less emission having $\lambda_{max}$ at about 460 nm with a quantum yield, $\phi$, in excess of 5% and a lifetime, τ, in excess of 1.5 μs. In embodiments of the invention, the blue emission of the bis-(NHC carbenes) alkylene ligand Pt(II) complex has a blue emission in dilute solution with a $\lambda_{max}$ less than 470 nm and a quantum yield greater than 5 percent. The bis-(NHC carbenes) alkylene ligand Pt(II) complex is a neutral square-planar Pt(II) complex, that is rigid and thermal stabile, wherein thermal decomposition occurs at temperatures above 280° C.

Figure 3:
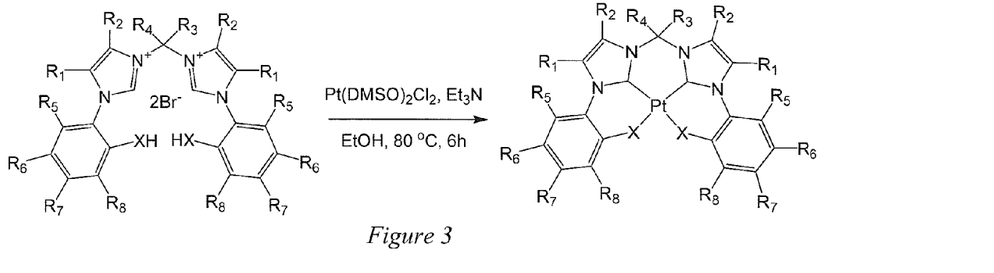
FIG. 3 shows a reaction scheme for the conversion of a tetradentate bis-(NHC carbene) ligand precursor to a tetradentate bis-(NHC carbene) ligand Pt(II) complex, according to an embodiment of the invention.

In an embodiment of the invention, the tetra-protonated bis-(NHC carbenes) alkylene ligand precursor is combined with a Pt(II) salt to form a tetradentate bis-(NHC carbenes) alkylene ligand Pt(II) complex, as illustrated in FIG. 3. The Pt(II) salt can be a solvated or unsolvated platinum halide or its equivalent. For example the dimethylsulfoxide solvated $PtCl_2$, $Pt(DMSO)_2Cl_2$ can be used. The complexation is carried out in solution in the presence of a proton acceptor, such as an amine. In an embodiment of the invention the proton acceptor is a tertiary amine, such as, but not limited to, trimethylamine, triethylamine, pyridine, N,N,N,N-tetramethylethylenediamine, or 1,4-dimethylpiperazine.

According to an embodiment of the invention, tetradentate bis-(NHC carbenes) alkylene ligand Pt(II) complexes are dispersed and immobilized in an inert polymer matrix, for example, but not limited to, poly(methyl methacrylate) (PMMA), to form a highly emissive film in the blue spectral region at a complex to polymer weight ratio of 1% or more. Absolute emission quantum yields for these films are around 30%, as measured with an integrate sphere method at room temperature. Emission maxima of the films can be blue-shifted by up to 10 nm from that for the bis-(NHC carbenes) alkylene ligand Pt(II) complexes in solution, suggesting a solid-solution state in the polymer dispersions. The films exhibit emission with chromaticity, as indicated by Commission Internationale de L'Eclairage coordinates, of $CIE_{x,y}$<0.2 and $CIE_{x+y}$<0.3. For example, complex 4, shown in FIG. 4, displays $CIE_{x,y}$ of (0.15, 0.10), which is nearly that considered to be an ideal deep blue, where $CIE_{x,y}$ of (0.14, 0.10).

All patents and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Materials and Methods

All starting materials were used as received from commercial sources. The solvents used for photophysical measurements were of HPLC grade. Elemental analyses were performed by the Institute of Chemistry at the Chinese Academy of Sciences, Beijing. Fast atom bombardment (FAB) mass spectra were obtained on a Finnigan Mat 95 mass spectrometer. $^1H$ (300 MHz or 400 MHz) NMR spectra were recorded on DPX300 and Avance400 Bruker FT-NMR spectrometers. UV-Vis spectra were recorded on a Perkin-Elmer Lambda 19 UV/vis spectrophotometer. Steady-state emission and excitation spectra at 298 K and Photoluminescence of films on quartz substrate were obtained on a Spex 1681 Fluorolog-2 Model F111 spectrophotometer equipped with a Hamamatsu R928 PMT detector. All solutions for photophysical measurements, except stated otherwise, were degassed in a high-vacuum line with at least four freeze-pump-thaw cycles. Emission lifetimes were measured with a Quanta-Ray Q-switch DCR-3 Nd:YAG pulsed laser system. Emission quantum yields were measured using a degassed acetonitrile solution of $[Ru(bpy)_3](PF_6)_2$ (bpy=2,2'-bipyridine) as the standard ($\phi_r$=0.062) and calculated by $\phi_s=\phi_r(B_r/B_s)(n_s/n_r)^2 (D_s/D_r)$, where the subscripts s and r refer to the sample and reference standard solution, respectively, n is the refractive index of the solvents, D is the integrated intensity, and φ is the luminescence quantum yield. The quantity B is calculated by $B=1-10^{-AL}$, where A is the absorbance at the excitation wavelength and L is the optical path length. Errors for wavelength values (1 nm) and φ (10%) are estimated.

4-Methyl-2-bromoanisole and 4-(tert-butyl)-2-bromoanisole were prepared from 4-Methyl-2-bromophenol and 4-(tert-butyl)-2-bromophenol by reaction with MeI in the presence of $K_2CO_3$ following literature procedure. (Lygo, *Tetrahedron Lett.*, 1999, 40, 1389)

4-methyl-2-bromoanisole

84% $^1$H-NMR (400 MHz, $CDCl_3$) δ (ppm) 7.36 (d, J=2.1 Hz, 1H), 7.05 (dd, J=8.3 Hz, 2.1 Hz, 1H), 6.79 (d, J=8.3 Hz, 1H), 3.86 (s, 3H), 2.28 (s, 3H)

4-(tert-butyl)-2-bromoanisole $^1$H-NMR (300 MHz, $CDCl_3$) δ(ppm) 7.54 (d, J=2.2 Hz, 1H), 7.27 (dd, J=8.6 Hz, 2.2 Hz, 1H), 6.83 (d, J=8.6 Hz, 1H), 3.87 (s, 3H), 1.28 (s, 9H).

2-(1H-imidazol-1-yl)anisole

To a degassed DMSO (20 mL) solution of imidazole (1.0 g, 15 mmol) was added 2-bromoanisole (1.25 mL, 10 mmol), KOH (1.12 g, 20 mmol) and $Cu_2O$ (280 mg, 2 mmol) under nitrogen. The resulting mixture was stirred at 140° C. for 24 hrs under $N_2$. After cooling to room temperature, the mixture was poured into ethylacetate (EA) (50 mL) and filtered. The filtrate was washed with water (50 mL×3) and dried over anhydrous magnesium sulfate. After rotary evaporation, the crude oil was purified via column chromatography on silica gel with eluent of EA/MeOH (9/1, v/v), affording a light yellow liquid (50%). $^1$H-NMR (400 MHz, $CDCl_3$) δ(ppm) 7.79 (s, 1H), 7.36 (t, J=7.8 Hz, 1H), 7.28 (d, J=7.8 Hz, 1H), 7.21 (s, 1H), 7.17 (s, 1H), 7.05 (m, 2H), 3.85 (s, 3H).

4-fluoro-2-(1H-imidazol-1-yl)anisole

To a degassed DMSO (20 mL) solution of imidazole (1.0 g, 15 mmol) was added 4-fluoro-2-bromoanisole (1.25 mL, 10 mmol), KOH (1.12 g, 20 mmol) and $Cu_2O$ (280 mg, 2 mmol) under nitrogen. The resulting mixture was stirred at 140° C. for 24 hrs under $N_2$. After cooling to room temperature, the mixture was poured into ethylacetate (EA) (50 mL) and filtered. The filtrate was washed with water (50 mL×3) and dried over anhydrous magnesium sulfate. After rotary evaporation, the crude oil was purified via column chromatography on silica gel with eluent of EA/MeOH (9/1, v/v), affording a light yellow liquid (47%). $^1$H-NMR (400 MHz, $CDCl_3$) δ(ppm) 7.82 (s, 1H), 7.21 (m, 1H), 7.17 (m, 1H), 7.07 (m, 2H), 7.00 (m, 1H), 3.84 (s, 3H).

4-methyl-2-(1H-imidazol-1-yl)anisole

To a degassed DMSO (20 mL) solution of imidazole (1.0 g, 15 mmol) was added 4-methyl-2-bromoanisole (1.25 mL, 10 mmol), KOH (1.12 g, 20 mmol) and $Cu_2O$ (280 mg, 2 mmol) under nitrogen. The resulting mixture was stirred at 140° C. for 24 hrs under $N_2$. After cooling to room temperature, the mixture was poured into ethylacetate (EA) (50 mL) and filtered. The filtrate was washed with water (50 mL×3) and dried over anhydrous magnesium sulfate. After rotary evaporation, the crude oil was purified via column chromatography on silica gel with eluent of EA/MeOH (9/1, v/v), affording a light yellow solid (57%). $^1$H-NMR (300 MHz, CDCl$_3$) δ(ppm) 7.78 (s, 1H), 7.16 (m, 3H), 7.09 (d, J=1.8 Hz, 1H), 6.94 (d, J=8.4 Hz, 1H), 3.81 (s, 3H), 2.33 (s, 3H).

4-t-butyl-2-(1H-imidazol-1-yl)anisole

To a degassed DMSO (20 mL) solution of imidazole (1.0 g, 15 mmol) was added 4-methyl-2-bromoanisole (1.25 mL, 10 mmol), KOH (1.12 g, 20 mmol) and Cu$_2$O (280 mg, 2 mmol) under nitrogen. The resulting mixture was stirred at 140° C. for 24 hrs under N$_2$. After cooling to room temperature, the mixture was poured into ethylacetate (EA) (50 mL) and filtered. The filtrate was washed with water (50 mL×3) and dried over anhydrous magnesium sulfate. After rotary evaporation, the crude oil was purified via column chromatography on silica gel with eluent of EA/MeOH (9/1, v/v), affording a light yellow oil with yield of 47%. $^1$H-NMR (400 MHz, CDCl$_3$) δ(ppm) 7.77 (s, 1H), 7.37 (dd, J$_1$=8.6 Hz, J$_2$=2.4 Hz, 1H), 7.27 (d, J=2.4 Hz, 1H), 7.21 (1H), 7.17 (1H), 6.99 (d, J=8.6 Hz, 1H), 3.82 (s, 3H), 1.32 (s, 9H).

1,1'-bis[(2-methoxyphenyl)-1H-imidazolium]-3,3'-methanediyl dibromide

A solution of 2-(1H-imidazol-1-yl)anisole (0.82 g, 4.7 mmol) and dibromomethane (1 mL, 14 mmol) in THF (5 mL) was refluxed at 110° C. for 48 hrs. After cooling to room temperature, the resulting white precipitate was collected by filtration with suction, washed with THF, and air-dried to yield 0.9 g of solids (73%). $^1$H-NMR (400 MHz, DMSO-d$_6$) δ(ppm) 10.01 (s, 2H), 8.30 (m, 2H), 8.22 (m, 2H), 7.64 (m, 4H), 7.41 (d, J=8.3 Hz, 2H), 7.22 (t, J=7.7 Hz, 2H), 6.90 (s, 2H), 3.90 (s, 6H).

1,1'-bis[(4-fluoro-2-methoxyphenyl)-1H-imidazolium]-3,3'-methanediyl dibromide

A solution of 4-fluoro-2-(1H-imidazol-1-yl)anisole (0.90 g, 4.7 mmol) and dibromomethane (1 mL, 14 mmol) in THF (5 mL) was refluxed at 110° C. for 48 hrs. After cooling to room temperature, the resulting white precipitate was collected by filtration with suction, washed with THF, and air-dried to yield a white solid with yield of 70%. $^1$H-NMR (400 MHz, MeOD) δ(ppm) 8.33 (d, J=2.1 Hz, 2H), 8.11 (d, J=2.1 Hz, 2H), 7.66 (m, 2H), 7.40 (m, 4H), 7.11 (s, 2H), 3.98 (s, 6H). Note: the imidazole NCHN signal do not appeared in MeOD solvent.

1,1'-bis[(4-methyl-2-methoxyphenyl)-1H-imidazolium]-3,3'-methanediyl dibromide

A solution of 4-methyl-2-(1H-imidazol-1-yl)anisole (0.88 g, 4.7 mmol) and dibromomethane (1 mL, 14 mmol) in THF (5 mL) was refluxed at 110° C. for 48 hrs. After cooling to room temperature, the resulting white precipitate was collected by filtration with suction, washed with THF, and air-dried to yield a white solid with yield of 70%. $^1$H-NMR (300 MHz, DMSO-d$_6$) δ(ppm) 9.93 (s, 2H), 8.26 (m, 2H), 8.20 (m, 2H), 7.47 (d, J=1.6 Hz, 2H), 7.44 (dd, J$_1$=8.6 Hz, J$_2$=1.6 Hz, 2H), 7.31 (d, J=8.6 Hz, 2H), 6.86 (s, 2H), 3.88 (s, 3H), 2.33 (s, 3H).

1,1'-bis[(4-t-butyl-2-methoxyphenyl)-1H-imidazolium]-3,3'-methanediyl dibromide

A solution of 4-t-butyl-2-(1H-imidazol-1-yl)anisole (1.08 g, 4.7 mmol) and dibromomethane (1 mL, 14 mmol) in THF (5 mL) was refluxed at 110° C. for 48 hrs. After cooling to room temperature, the resulting white precipitate was collected by filtration with suction, washed with THF, and air-dried to yield a white solid with yield of 74%. $^1$H-NMR (400 MHz, DMSO-d$_6$) δ(ppm) 10.00 (s, 2H), 8.31 (m, 2H), 8.24 (m, 2H), 7.64 (m, 4H), 7.33 (d, J=8.8 Hz, 2H), 6.89 (s, 2H), 3.89 (s, 3H), 1.28 (s, 18H).

1,1'-bis[(2-hydroxyphenyl)-1H-imidazolium]-3,3'-methanediyl dibromide

A solution of 1,1'-bis[(2-methoxyphenyl)-1H-imidazolium]-3,3'-methanediyl dibromide (0.81 g, 1.55 mmol) in HBr (48 wt. % aq. 6.5 mL)/HOAc (6.5 mL) was heated to reflux at 120° C. for 48 hrs. After reaction, the mixture was rotary evaporated. Acetone was added to the residue to induce precipitation of brown solids, which were collected by filtration and washed with EA. After reprecipitation from DMF/EA, a white solid was obtained (0.52 g, 68%). $^1$H-NMR (400 MHz, DMSO-d$_6$) δ(ppm) 11.08 (br s, 2H), 9.99 (s, 2H), 8.29 (s, 2H), 8.22 (s, 2H), 7.57 (d, J=7.86 Hz, 2H), 7.44 (t, J=7.77 Hz, 2H), 7.19 (d, J=8.13 Hz, 2H), 7.06 (t, J=7.58 Hz, 2H), 6.90 (s, 2H).

1,1'-bis[(4-fluoro-2-hydroxyphenyl)-1H-imidazolium]-3,3% methanediyl dibromide (1)

A solution of 1,1'-bis[(4-fluoro-2-methoxyphenyl)-1H-imidazolium]-3,3'-methanediyl dibromide (0.87 g, 1.55 mmol) in HBr (48 wt. % aq. 6.5 mL)/HOAc (6.5 mL) was heated to reflux at 120° C. for 48 hrs. After reaction, the mixture was rotary evaporated. Acetone was added to the residue to induce precipitation of brown solids, which were collected by filtration and washed with EA. After reprecipitation from MeOH/EA, a white solid was obtained with yield of 84% $^1$H-NMR (300 MHz, MeOD) δ(ppm) 9.97 (im NCHN, s, active), 8.23 (d, J=2.0 Hz, 2H), 8.13 (d, J=2.0 Hz, 2H), 7.52 (dd, J$_1$=8.4 Hz, J$_2$=3.0 Hz, 2H), 7.26 (td, J$_1$=9.0 Hz, J$_2$=3.0 Hz, 2H), 7.14 (dd, J$_1$=9.0 Hz, J$_2$=4.8 Hz, 2H), 7.00 (s, 2H).

1,1'-bis[(4-methyl-2-hydroxyphenyl)-1H-imidazolium]-3,3%-methanediyl dibromide (2)

A solution of 1,1'-bis[(4-methyl-2-methoxyphenyl)-1H-imidazolium]-3,3'-methanediyl dibromide (0.85 g, 1.55 mmol) in HBr (48 wt. % aq. 6.5 mL)/HOAc (6.5 mL) was heated to reflux at 120° C. for 48 hrs. After reaction, the mixture was rotary evaporated. Acetone was added to the residue to induce precipitation of brown solids, which were collected by filtration and washed with EA. After reprecipitation from MeOH/EA, a white solid was obtained with yield of 65% $^1$H-NMR (300 MHz, DMSO-d$_6$) δ(ppm) 10.82 (br s, 2H), 9.96 (s, 2H), 8.28 (m, 2H), 8.20 (m, 2H), 7.39 (d, J=1.6 Hz, 2H), 7.25 (dd, J$_1$=8.4 Hz, J$_2$=1.6 Hz, 2H), 7.08 (d, J=8.4 Hz, 2H), 6.88 (s, 2H), 2.28 (s, 6H). (300 MHz, MeOD) δ(ppm) 9.91 (im NCHN, s, 2H), 8.20 (m, 2H), 8.09 (m, 2H), 7.43 (d, J=1.6 Hz, 2H), 7.28 (dd, J$_1$=8.4 Hz, J$_2$=1.6 Hz, 2H), 7.03 (d, J=8.4 Hz, 2H), 6.98 (s, 2H), 2.35 (s, 6H).

1,1'-bis[(4-t-butyl-2-hydroxyphenyl)-1H-imidazolium]-3,3% methanediyl dibromide (3)

A solution of 1,1'-bis[(4-t-butyl-2-methoxyphenyl)-1H-imidazolium]-3,3'-methanediyl dibromide (0.98 g, 1.55 mmol) in HBr (48 wt. % aq. 6.5 mL)/HOAc (6.5 mL) was heated to reflux at 120° C. for 48 hrs. After reaction, the mixture was rotary evaporated. Acetone was added to the residue to induce precipitation of brown solids, which were collected by filtration and washed with EA. After reprecipitation from DMF/EA, a white solid was obtained with yield of 62%. $^1$H-NMR (400 MHz, DMSO) δ(ppm) 10.85 (s, 2H), 9.91 (s, 2H), 8.24 (m, 4H), 7.48 (m, 4H), 7.11 (d, J=8.4 Hz), 6.84 (s, 2H), 1.29 (s, 18H).

Bis[3,3'-(2-phenoxide)-1H-imidazolium-2,2'-diylidene]-methane-1,1'-diyl-platinum(II) (7)

A mixture of 1,1'-bis[(2-hydroxyphenyl)-1H-imidazolium]-3,3'-methanediyl dibromide (193 mg, 0.39 mmol), Pt(DMSO)$_2$Cl$_2$ (164 mg, 0.39 mmol) and Et$_3$N (0.325 mL, 6 eq.) in EtOH (20 mL) was heated to 80° C. for 6 hrs. After completion of reaction, the mixture was cooled to room temperature, collected by centrifugation, washed with ethanol, ether and was dried under vacuum, affording pale yellow solids (60%). $^1$H-NMR (400 MHz, DMSO-d$_6$) δ(ppm) 8.34 (d, J=2.3 Hz, 2H), 7.71 (d, J=2.3 Hz, 2H), 7.69 (d, J=8.35 Hz, 2H), 7.06 (t, J=7.65 Hz, 2H), 6.92 (d, J=8.27 Hz, 2H), 6.57 (t, J=7.57 Hz, 2H), 6.31 (s, 2H) FAB-MS: 526.0 [M+H]$^+$. Anal. Calcd. For C$_{19}$H$_{14}$N$_4$O$_2$Pt.H$_2$O: C, 41.99; H, 2.97; N, 10.31. Found: C, 42.06; H, 2.88; N, 9.99.

Bis[3,3'-(4-fluoro-2-phenoxide)-1,1-imidazolium-2,2'-diylidene]-methane-1,1'-diyl-platinum(II) (4)

A mixture of 1 (207 mg, 0.39 mmol), Pt(DMSO)$_2$Cl$_2$ (164 mg, 0.39 mmol) and Et$_3$N (0.325 mL, 6 eq.) in EtOH (20 mL) was heated to 80° C. for 6 hrs. After completion of reaction, the mixture was cooled to room temperature, collected by centrifugation, washed with ethanol, ether and was dried under vacuum, affording white solids with yield of 49%. $^1$H-NMR (400 MHz, DMSO-d$_6$) δ(ppm) 8.34 (d, J=1.8 Hz, 2H), 7.72 (d, J=1.8 Hz, 2H), 7.66 (d, J=10.5 Hz, 2H), 6.90 (m, 4H), 6.32 (s, 2H) FAB-MS: 561.0 [M+H]$^+$. Anal. Calcd. For C$_{19}$H$_{12}$N$_4$O$_2$Pt.H$_2$O: C, 39.38; H, 2.44; N, 9.67. Found: C, 38.77; H, 2.40; N, 9.35.

Bis[3,3'-(4-methyl-2-phenoxide)-1H-imidazolium-2,2'-diylidene]-methane-1,1'-diyl-platinum(II) (5)

A mixture of 2 (204 mg, 0.39 mmol), Pt(DMSO)$_2$Cl$_2$ (164 mg, 0.39 mmol) and Et$_3$N (0.325 mL, 6 eq.) in EtOH (20 mL) was heated to 80° C. for 6 hrs. After completion of reaction, the mixture was cooled to room temperature, collected by centrifugation, washed with ethanol, ether and was dried under vacuum, affording white solids with yield of 56%. $^1$H-NMR (300 MHz, DMSO-d$_6$) δ(ppm) 8.31 (d, J=2.1 Hz, 2H), 7.69 (d, J=2.1 Hz, 2H), 7.51 (s, 2H), 6.87 (d, J=8.2 Hz, 2H), 6.80 (d, J=8.2 Hz, 2H), 6.29 (s, 2H), 2.25 (s, 6H) FAB-MS: 553.0 [M+H]$^+$. Anal. Calcd. For C$_{21}$H$_{18}$N$_4$O$_2$Pt.CH$_2$Cl$_2$: C, 41.39; H, 3.16; N, 8.78. Found: C, 41.38; H, 3.22; N, 8.82.

Figure 5:
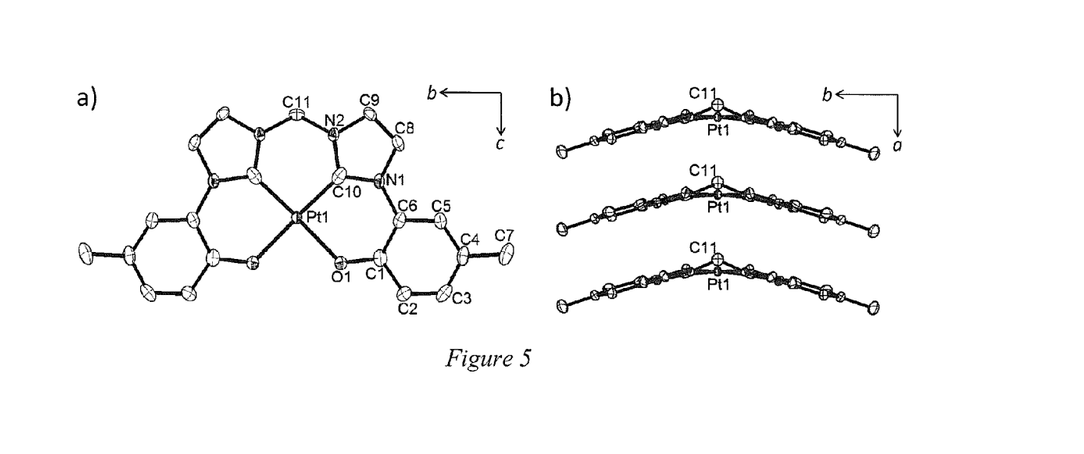
FIG. 5 shows the X-ray crystal structure of complex 5, according to an embodiment of the invention: a) as a perspective view with thermal ellipsoids in 50% probability and hydrogen atoms and solvated molecules omitted for clarity; and b) the packing diagram viewed along c-axis.

A single-crystal of 5 suitable for X-ray diffraction analysis was obtained from a dilute solution in dichloromethane upon slow evaporation of the solvent in the presence of air. The complex crystallized into an orthorhombic space group, as indicated in Table 1, below. As can be seen in FIG. 5a, Complex 5 has a C$_2$-symmetry along the Pt1-C11 axis. The four bond angles around Pt(II) are within 90±2°, indicating a square-planar coordination geometry with a negligible strain in the tetradentate ligand accommodating the Pt(II) ion. The Pt—C(NHC) distances of 1.93 Å are shorter than those found in tetra(NHC)—Pt(II) (2.03 Å) and bis(NHC)—Pt(II) acetylide (1.98 Å) complexes, indicating strong Pt—C(NHC) bonding interactions. The Pt—O(phenolate) distances of 2.05 Å are slightly longer those found in Salphen-Pt(II) (1.99 Å) and (N$_2$O$_2$)—Pt(II) (1.98 Å) complexes, probably due to weak Pt—O(phenolate) bonds induced by the strong trans-effect of the NHC moieties. The molecules of 5 adopt a bent framework due to the non-conjugated C11 methylene linker between the two NHC moieties, and these bent molecules stack into infinite columns in a head-to-tail cofacial manner with intermolecular π-π distances of 3.5 Å along a-axis, as shown in FIG. 5b. A solvated water molecule is hydrogen-bonded to the two phenolate oxygen atoms of a complex molecule. Disordered solvating dichloromethane molecules are located in the channels between the columns formed by the stacked 5 molecules.

TABLE 1

| Crystal Data of complex 3 | |
|---|---|
| formula | C$_{22}$H$_{22}$Cl$_2$N$_4$O$_3$Pt |
| fw | 656.43 |
| color | Colorless |
| crystal size | 0.1 × 0.04 × 0.02 |
| crystal system | Orthorhombic |
| space group | Pnma |
| a, Å | 6.7618(2) |
| b, Å | 24.1817(7) |
| c, Å | 13.4445(4) |
| α, deg | 90 |
| β, deg | 90 |
| γ, deg | 90 |
| V, Å$^3$ | 2198.33 |
| Z | 4 |
| D$_c$, g cm$^{-3}$ | 1.983 |
| μ, cm$^{-1}$ | 14.461 |
| F(000) | 1272 |
| 2θ$_{max}$, deg | 130.81 |
| no. unique data | 1872 |
| no. obsd. data | |
| GOF | 1.191 |
| for I > 2σ (I) | |
| no. variables | 155 |
| R$^a$ | 0.0517 |
| Rw$^b$ | 0.0968 |
| residual ρ, e Å$^{-3}$ | 1.364, -2.386 |

$^a$R = Σ||F$_o$| - |F$_c$||/Σ|F$_o$|.
$^b$R$_w$ = [Σ w (|F$_o$| - |F$_c$|)$^2$/Σ w |F$_o$|$^2$]$^{1/2}$.

Bis[3,3'-(4-t-butyl-2-phenoxide)-1,1-imidazolium-2,2'-diylidene]-methane-1,1'-diyl-platinum(II) (6)

A mixture of 3 (237 mg, 0.39 mmol), Pt(DMSO)$_2$Cl$_2$ (164 mg, 0.39 mmol) and Et$_3$N (0.325 mL, 6 eq.) in EtOH (20 mL) was heated to 80° C. for 6 hrs. After completion of reaction, the mixture was cooled to room temperature, collected by centrifugation, washed with ethanol, ether and was dried under vacuum, affording white solids with yield of 58%. $^1$H-NMR (400 MHz, DMSO-d$_6$) δ(ppm) 8.42 (d, 2.3 Hz, 2H), 7.71 (d, 2.3 Hz, 2H), 7.52 (d, J=2.3 Hz, 2H), 7.08 (dd, J$_1$=8.6 Hz, J$_2$=2.3 Hz, 2H), 6.83 (d, J=8.6 Hz, 2H), 6.30 (s, 2H), 1.29 (s, 18H) FAB-MS: 638.2 [M+H]$^+$. Anal. Calcd. For C$_{27}$H$_{30}$N$_4$O$_2$Pt.H$_2$O: C, 49.46; H, 4.92; N, 8.55. Found: C, 49.36; H, 4.64; N, 8.46.

Figure 6:
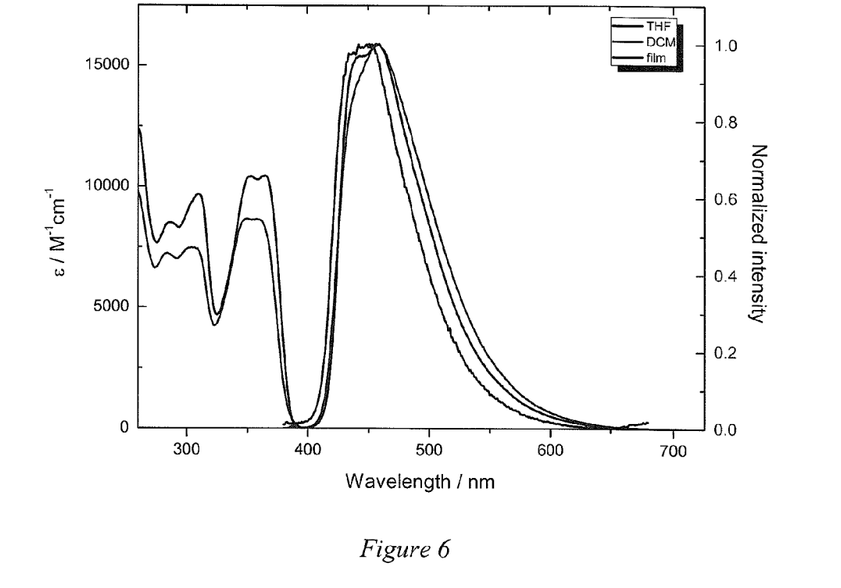
FIG. 6 shows absorption and emission spectra of 4, with absorption below 382 and emission above 382, for a dichloromethane-DMF solution (19:1, v/v), THF-DMF solution (19:1, v/v) (blue shifted), and a film of 4 in poly(methylmethacrylate) (1 wt %) (emission only and further blue shifted), according to an embodiment of the invention.
Figure 7:
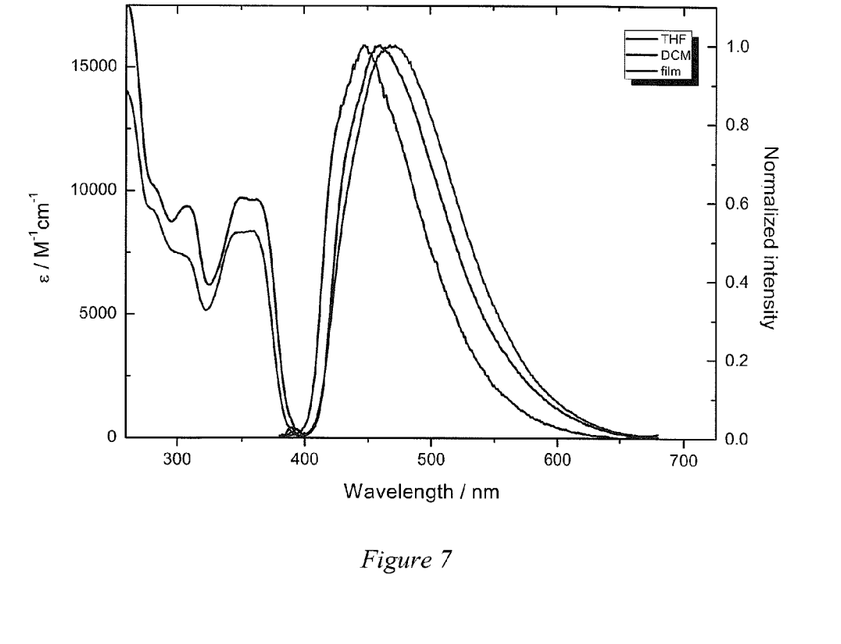
FIG. 7 shows absorption and emission spectra of 5, with absorption below 382 and emission above 382, for a dichloromethane-DMF solution (19:1, v/v), THF-DMF solution (19:1, v/v) (blue shifted), and a film of 5 in poly(methylmethacrylate) (1 wt %) (emission only and further blue shifted), according to an embodiment of the invention.
Figure 8:
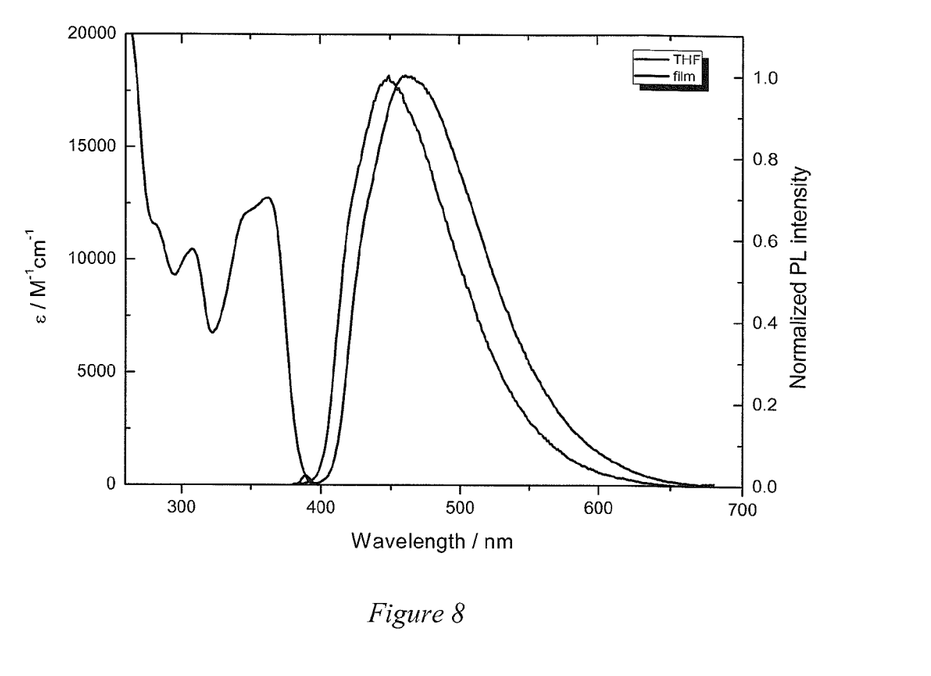
FIG. 8 shows absorption and emission spectra of 6, with absorption below 382 and emission above 382, for a THF-DMF solution (19:1, v/v) (blue shifted), and a film of 6 in poly(methylmethacrylate) (1 wt %) (emission only and blue shifted), according to an embodiment of the invention.

Absorption and emission spectra were acquired for complexes 4-7, as summarized in Table 2, below, solution measurements were performed using THF-DMF (19:1, v/v) solutions. All of the complexes show a vibronically structured absorption band with peak maxima at about 350 nm and molar extinction coefficients of about 1×10$^4$ M$^{-1}$ cm$^{-1}$. In solution, complexes 5 and 6 display structure-less emissions centered at around 460 nm with quantum yields of 8% and lifetimes of 1.8 μs, which is significantly greater than that for 7, the complex from an unsubstituted ligand. A blue-shifted emission maximum at 443 nm with a high quantum yield of 18% and long lifetime of 3.5 μs was observed in solution for complex 4 with an electron-drawing fluoride group para to the phenolate oxygen. A red-shift of 5 nm for the emission maxima for 4-7 was observed upon changing solvent from THF-DMF to dichloromethane-DMF (19:1, v/v). Representative adsorption and emission spectra for 4-6 are shown in FIGS. 6-8 respectively.

Complexes 4-7 are highly emissive in the blue spectral region when measured in films prepared by the dispersion of a complex in an inert polymer matrix, poly(methyl methacrylate) (PMMA) in these exemplary examples, at a complex to polymer weight ratio as low as 1%. Absolute emission quantum yields for these solid films, measured by an integrate sphere method, were observed to be approximately 30%, within experimental error, at room temperature for 4-7 with emission maxima blue-shifted by 10 nm from that recorded for the complexes in THF-DMF solution, which suggests a solid-solution state within the film. All of the films exhibit emission with a chromaticity of $CIE_{x,y} < 0.2$ ($CIE_{x,y} =$ Commission Internationale de L'Eclairage coordinates) and $CIE_{x+y} < 0.3$, and particularly, films of complex 4 gave $CIE_{x,y}$ at (0.15, 0.10), being close to an ideal deep blue with $CIE_{x,y}$ at (0.14, 0.10).

TABLE 2

Photophysical data of complexes 4-7.

| | Absorption[a] $\lambda_{max}$ in nm ($\epsilon$ in M$^{-1}$cm$^{-1}$) | Emission[a] $\lambda_{max}$ (nm); τ (μs); φ (%) | Emission[b] $\lambda_{max}$/nm; φ |
|---|---|---|---|
| 4 | 286 (8.5), 310 (9.7), 353 (10.4), 365 (10.5) | 443, 459; 3.5; 18% | 434, 451; 26% |
| 5 | 284 (10.0), 308 (9.4), 351 (9.7), 362 (9.7) | 460; 1.8; 7% | 448; 24% |
| 6 | 282 (11.5), 308 (10.5), 352 (12.3), 363 (12.7) | 461; 1.8; 8% | 449; 26% |
| 7 | 277 (8.4), 302 (7.3), 342 (7.1), 353 (7.1) | 457; 0.5; 3% | 443; 29% |

[a]Recorded in degassed THF-DMF (19:1, v/v) solutions with a concentration of ~2 × 10$^{-5}$ M, absorption at about 305 is a shoulder, and $\lambda_{ex}$ for emissions is 350 nm.
[b]Recorded in 1% PMMA film and $\lambda_{ex}$ for emissions is 350 nm.

Figure 9:
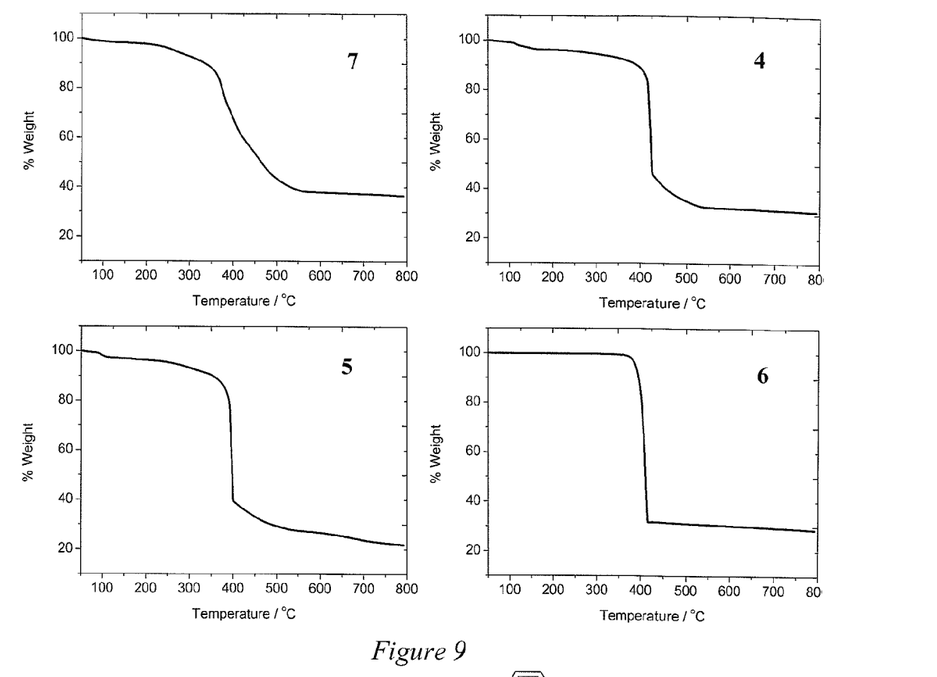
FIG. 9 shows thermal gravimetric plots for complexes 4-7, according to an embodiment of the invention.

Decomposition temperatures of 4-6 under a nitrogen atmosphere are 410, 390, and 400° C., respectively, as determined by thermogravimetric analyses, as shown in FIG. 9. Complexes 4-6 meet the prerequisite for thermal deposition of these complexes in OLED fabrications and exceeds that of unsubstituted complex 7 which decomposed beginning at 250° C.

Complex 6 was used as phosphorescent dopant in a blue OLED. The device configuration is ITO/2-TNATA (40 nm)/ NPB (20 nm)/DP4-Pt 3% (30 nm)/TPBi (40 nm)/LiF (0.5 nm)/Al (100 nm). 2-TNATA, NPB and TPBi were used as hole-injection layer (HIL), hole-transporting layer (HTL) and electron-transporting layer (ETL), respectively. The host DP4 was obtained from Aglaia Tech. Beijing, China, and its chemical structure cannot be revealed due to patent consideration. All materials were thermal-deposited in high vacuum in succession without breaking the vacuum. After finishing the whole deposition, the device was encapsulated with glass cap and tested at ambient conditions. The electroluminescence was recorded by a PR650-spectrometer and K2400 as the voltage source.

Figure 10:
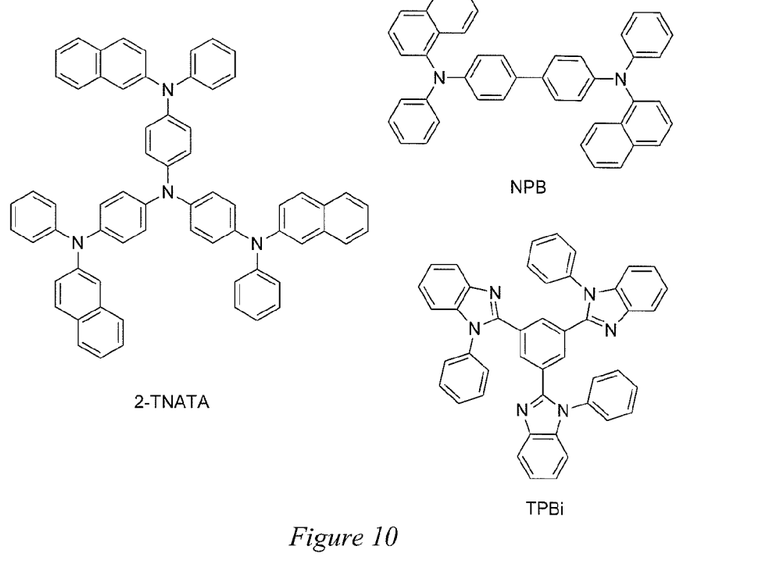
FIG. 10 shows the chemical structure of NPB, 2-TNATA, and TPBi, which are used for the construction of an exemplary OLED with an emissive layer comprising 5, according to an embodiment of the invention.
Figure 11:
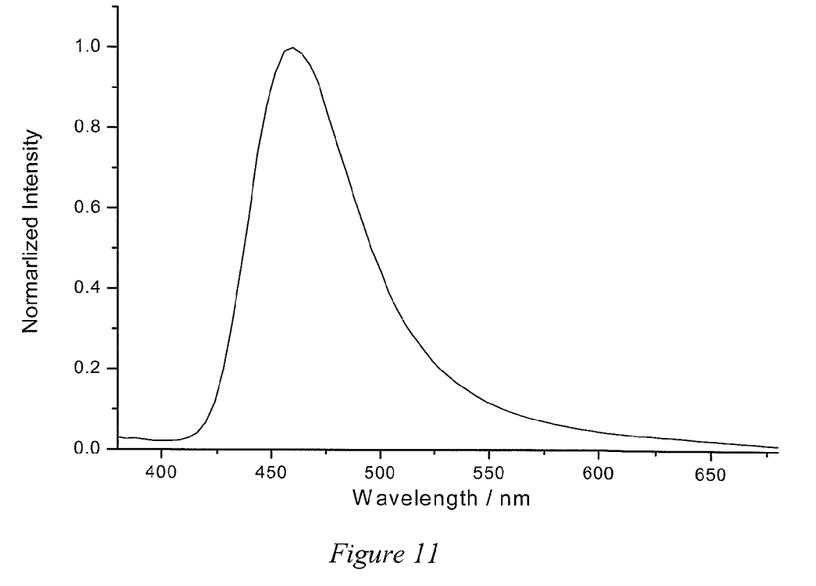
FIG. 11 shows an electroluminescence spectrum for the exemplary OLED with an emissive layer comprising 5, according to an embodiment of the invention.
Figure 12:
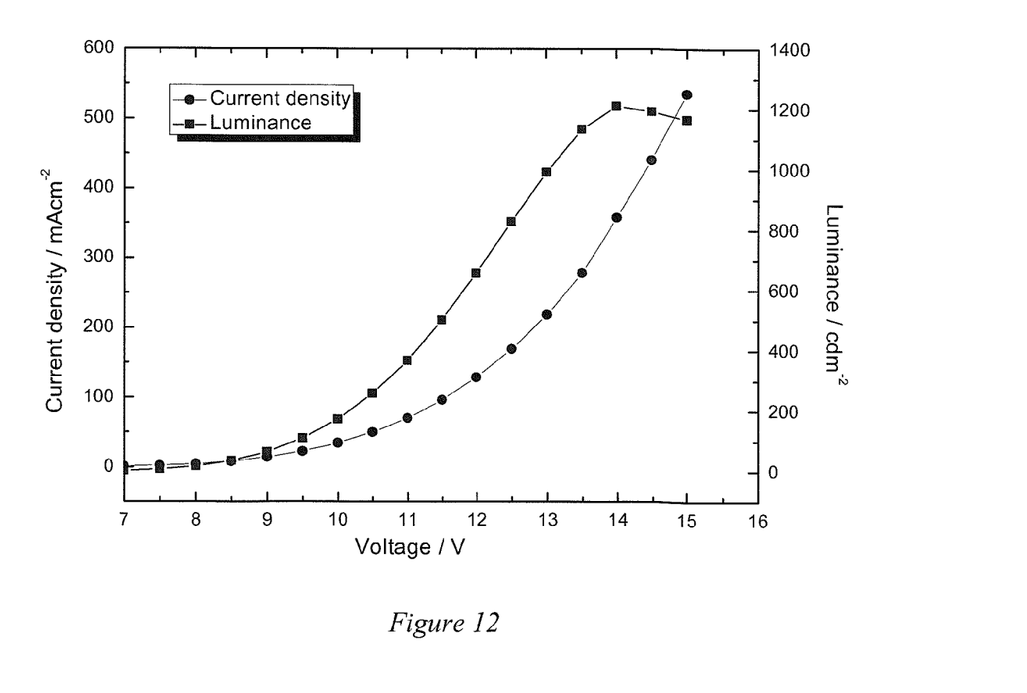
FIG. 12 shows a JVB cure for the exemplary OLED with an emissive layer comprising 5, according to an embodiment of the invention.

An OLED was fabricated using 6, which was vacuum-deposited as a dopant into the emitting layer of an OLED with a configuration of ITO/2-TNATA (40 nm)/NPB (20 nm)/ DP4-Complex 102 (30 nm)/TPBi (40 nm)/LiF (0.5 nm)/Al (100 nm). 2-TNATA, NPB and TPBi, whose structures are shown in FIG. 10, were used as hole-injection, hole-transporting and electron-transporting layer, respectively. Complex 6 was co-deposited with a broad-gap host (DP4, provided by Aglaia Tech., Beijing, China) at a 3 wt % doping level. The electroluminescence spectrum and JVB curve of the device are illustrated in FIGS. 11 and 12, respectively. A maximum brightness of 1200 cd/m$^2$ was recorded at a driving voltage of 15 V. The chromaticity of this device at 11 V is $CIE_{x,y}$ (0.16, 0.16), falling well into the blue spectral region. A peak luminous efficiency of 0.5 cd/A was recorded at 11 V.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A tetradentate bis-(NHC carbenes) alkylene ligand Pt(II) complex, comprising the structure:

(II)

wherein $R_1$-$R_8$ are independently hydrogen, fluoro, chloro, bromo, iodo, alkyl, substituted alkyl, cycloalkyl, or substituted cycloalkyl;

wherein at least one of $R_1$-$R_8$ is not hydrogen; and wherein X is O.

2. The tetradentate bis-(NHC carbenes) alkylene ligand Pt(II) complex of claim 1, wherein $R_6$ or $R_8$ is substituted with an electron withdrawing substituent.

3. The tetradentate bis-(NHC carbenes) alkylene ligand Pt(II) complex of claim 1, wherein the tetradentate ligand Pt(II) complex has a blue emission with a maximum less than 470 nm.

4. The tetradentate bis-(NHC carbenes) alkylene ligand Pt(II) complex of claim 3, wherein the tetradentate ligand Pt(II) complex has the blue emission with a quantum efficiency in solution of at least 5 percent.

5. The tetradentate bis-(NHC carbenes) alkylene ligand Pt(II) complex of claim 1, of the structure:

6. A method for the preparation of the tetradentate bis-(NHC carbenes) alkylene ligand Pt(II) complex of claim 1, comprising combining a precursor of a tetradentate ligand, comprising the structure:

wherein $R_1$-$R_8$ are independently hydrogen, fluoro, chloro, bromo, iodo, hydroxyl, alkyl, substituted alkyl, cycloalkyl, or substituted cycloalkyl; wherein at least one of $R_1$-$R_8$ is not hydrogen; wherein X is independently O; and wherein $A^-$ is chloride, bromide, iodide, tosylate, brosylate, triflate, or other anion of low nucleophilicity; with a Pt(II) salt in the presence of a proton acceptor in solution.

7. The method of claim 6, wherein the proton acceptor is a tertiary amine.

8. The method of claim 6, wherein the Pt(II) salt is a Pt(II) halide.

9. The method of claim 6, wherein the Pt(II) halide is $Pt(DMSO)_2Cl_2$.

10. An organic light-emitting diode (OLED), comprising an electroluminescence layer comprising a tetradentate bis-(NHC carbenes) alkylene ligand Pt(II) complex of claim 1.

11. An organic light-emitting diode (OLED) of claim 10, wherein the tetradentate bis-(NHC carbenes) alkylene ligand Pt(II) complex has a structureless blue emission in dilute solution having a $\lambda_{max}$ less than 470 nm with a quantum yield, ϕ, greater than 5%.

* * * * *

UNITED STATES PATENT AND TRADEMARK OFFICE
CERTIFICATE OF CORRECTION

PATENT NO. : 8,957,217 B2
APPLICATION NO. : 13/482448
DATED : February 17, 2015
INVENTOR(S) : Chi Ming Che and Kai Li It is certified that error appears in the above-identified patent and that said Letters Patent is hereby corrected as shown below:

In the specification

Column 1,
Line 44-45, "complex were" should read --complexes were--

Column 4,
Line 46, "-disubstituted" should read --di-substitute--

Column 5,
Line 7, "thermal stabile" should read --thermally stable--

Column 7,
Line 52, "signal do not appeared" should read --signal did not appear--

Column 8,
Line 29, "-3,3%" should read --3,3'--
Line 46, "-3,3%" should read --3,3'--
Line 55, "65% $^1$H-NMR" should read --65%. $^1$H-NMR--
Line 63, "-3,3%" should read --3,3'--

Column 9,
Line 25, "PT.H$_2$O" should read --PT·H$_2$O--
Line 28, "1,1-imidazolium" should read --1H-imidazolium--
Line 40, "PT.H$_2$O" should read --PT·H$_2$O--
Line 56, "PT.H$_2$O" should read --PT·H$_2$O--

Column 10,
Line 47, "1,1-imidazolium" should read --1H-imidazolium--
Line 60, "PT.H$_2$O" should read --PT·H$_2$O--

Signed and Sealed this
Tenth Day of November, 2015

Michelle K. Lee
*Director of the United States Patent and Trademark Office*

Line 12, "along a-axis" should read --along the a-axis--

Column 11,
Line 7, "fluoride group para" should read --fluoride group *para*--
Line 48, "as deteunined" should read --as determined--
Line 64-65, "with glass cap" should read --with a glass cap--